(12) United States Patent
Studer et al.

(10) Patent No.: US 8,057,546 B2
(45) Date of Patent: Nov. 15, 2011

(54) INTERVERTEBRAL DISK PROSTHESIS OR ARTIFICIAL VERTEBRAL BODY

(75) Inventors: Armin Studer, Cham (CH); Mario Gago, Basel (CH); Jason Trachsel, Biel (CH)

(73) Assignee: Synthes USA, LLC, West Chester, PA (US)

( * ) Notice: Subject to any disclaimer, the term of this patent is extended or adjusted under 35 U.S.C. 154(b) by 1012 days.

(21) Appl. No.: 11/542,536

(22) Filed: Oct. 2, 2006

(65) Prior Publication Data
US 2007/0067038 A1  Mar. 22, 2007

Related U.S. Application Data

(63) Continuation of application No. PCT/CH2004/000210, filed on Apr. 2, 2004.

(51) Int. Cl.
*A61F 2/44* (2006.01)
(52) U.S. Cl. ............... 623/17.11; 623/17.13; 623/17.15
(58) Field of Classification Search .... 623/17.11–17.16; 606/279
See application file for complete search history.

(56) References Cited

U.S. PATENT DOCUMENTS

| | | | |
|---|---|---|---|
| 4,309,777 A * | 1/1982 | Patil .......................... | 623/17.13 |
| 4,759,766 A | 7/1988 | Buettner-Janz et al. | |
| 4,759,769 A | 7/1988 | Hedman et al. ................ | 623/17 |
| 4,932,975 A | 6/1990 | Main et al. | |
| 5,320,644 A | 6/1994 | Baumgartner | |
| 5,714,694 A * | 2/1998 | Diessner .................. | 73/862.632 |
| 5,989,291 A * | 11/1999 | Ralph et al. ................ | 623/17.15 |
| 6,231,609 B1 * | 5/2001 | Mehdizadeh .............. | 623/17.11 |
| 6,375,682 B1 * | 4/2002 | Fleischmann et al. ..... | 623/17.12 |
| 6,579,320 B1 * | 6/2003 | Gauchet et al. ............ | 623/17.15 |
| 6,719,796 B2 * | 4/2004 | Cohen et al. ................ | 623/17.15 |
| 6,733,532 B1 | 5/2004 | Gauchet et al. | |
| 6,770,094 B2 * | 8/2004 | Fehling et al. ............. | 623/17.13 |
| 6,981,989 B1 * | 1/2006 | Fleischmann et al. ..... | 623/17.11 |
| 6,984,246 B2 * | 1/2006 | Huang ........................ | 623/17.13 |

(Continued)

FOREIGN PATENT DOCUMENTS

FR            2734148         11/1996

(Continued)

OTHER PUBLICATIONS

Notice of the Reasons for the Rejection issued by the Japanese Patent Office including an English Translation.

*Primary Examiner* — Thomas C. Barrett
*Assistant Examiner* — Matthew Lawson
(74) *Attorney, Agent, or Firm* — Stradley Ronon Stevens & Young, LLP

(57) ABSTRACT

An intervertebral disk prosthesis or the intervertebral implant has a cavity-like middle part with a longitudinal axis, an upper end, a lower end, an upper apposition plate, and a lower apposition plate. The upper apposition plate is placed on the upper end of the middle part such that it is perpendicular to the longitudinal axis. The upper apposition plate is suited for resting against the base plate of a vertebral body. The lower apposition plate is placed on the lower end of the middle part such that it is perpendicular to the longitudinal axis. The lower apposition plate is suited for resting against the cover plate of a vertebral body. The middle part has at least two coaxially arranged plate springs, which gives the middle part a progressive spring characteristic.

4 Claims, 2 Drawing Sheets

U.S. PATENT DOCUMENTS

| | | | |
|---|---|---|---|
| 7,250,060 B2 * | 7/2007 | Trieu | 623/17.15 |
| 7,429,270 B2 | 9/2008 | Baumgartner et al. | 623/17.12 |
| 7,758,645 B2 * | 7/2010 | Studer | 623/17.13 |
| 2003/0009223 A1 * | 1/2003 | Fehling et al. | 623/17.13 |
| 2003/0065395 A1 * | 4/2003 | Ralph et al. | 623/17.13 |
| 2003/0069642 A1 * | 4/2003 | Ralph et al. | 623/17.13 |
| 2004/0010316 A1 | 1/2004 | William et al. | |
| 2004/0034423 A1 | 2/2004 | Lyons et al. | |
| 2004/0249462 A1 * | 12/2004 | Huang | 623/17.13 |
| 2005/0107881 A1 * | 5/2005 | Alleyne et al. | 623/17.15 |
| 2005/0251260 A1 * | 11/2005 | Gerber et al. | 623/17.13 |
| 2006/0009850 A1 * | 1/2006 | Frigg et al. | 623/17.13 |

FOREIGN PATENT DOCUMENTS

| | | |
|---|---|---|
| WO | WO 2004/016217 | 2/2004 |
| WO | WO 2004/016217 A2 * | 2/2004 |

* cited by examiner

INTERVERTEBRAL DISK PROSTHESIS OR ARTIFICIAL VERTEBRAL BODY

CROSS-REFERENCE TO RELATED APPLICATION

This is a continuation of pending International Application No. PCT/CH2004/000210, filed Apr. 2, 2004, the entire contents of which are expressly incorporated herein by reference thereto.

FIELD OF THE INVENTION

The invention relates to a prosthetic intervertebral disk or an artificial vertebral body.

BACKGROUND OF THE INVENTION

Intervertebral disks comprising two apposition plates with a compression spring element in between are known. A hollow cylindrical jacket is typically arranged around the compression spring element. The compression spring element is usually made of a memory metal alloy which has superelastic properties at body temperature, or in other embodiments, the compression spring element includes a cup spring column made up of cup springs having the same stiffness. One disadvantage of these known prosthetic intervertebral disks is the linear spring characteristic of the compression spring element, so that in the case of a compression spring element which should also absorb impact forces, the flexibility of the compression spring element is too low, in particular at low compressive forces. Therefore the freedom of mobility of the spinal column is limited in this area.

SUMMARY OF THE INVENTION

The present invention seeks to remedy this situation. The invention is based on the object of creating a prosthetic intervertebral disk and/or an artificial vertebral body having an elastic middle part assembled from conventional elements and having a progressive spring characteristic.

This object is achieved by the present invention with a prosthetic intervertebral disk or an artificial vertebra having a middle part, an upper apposition plate, and a lower apposition plate. The middle part has elastic means which has a progressive spring characteristic.

The advantages of the present invention include:
sufficiently great elastic flexibility and damping in the case of low compressive forces; this ensures adequate freedom of mobility of the spinal column in this area;
no great spring deflections required to absorb the compressive force at high pressure or impact loads; and
the jump in stiffness between a healthy vertebral segment and the vertebral segment provided with a prosthesis may be reduced in a harmonious manner so as to yield a prosthesis that behaves like a healthy intervertebral disk.

In a preferred embodiment, the elastic means include at least two cup springs arranged coaxially.

In a special embodiment, centering is provided for the elastic means. Because of the centering, the cup springs cannot slip and are held in their positions. Furthermore, because of the centering, the adjacent cup springs may absorb very high forces and may serve as a security means.

In another embodiment, the centering is designed to be flexible, so that it permits an axial guidance within a conical area. The advantage achieved here is that not only is the prosthetic intervertebral disk designed to be elastic coaxially, but also the apposition plates may be moved obliquely or rotationally in relation to one another.

In still another embodiment, the cup springs have central bores and the centering is designed as internal bellows passing through these bores.

In yet another embodiment, at least two cup springs have a different stiffness. Therefore, the progressive spring characteristic can be established by the spring having only cup springs. Another advantage is the large supporting surface, which results in low surface pressure and low abrasion.

In a further embodiment, the cup springs are combined to form cup spring assemblies having several stacked parallel cup springs. This has the advantage that the progressive spring characteristic can be created only through a spring consisting of cup springs. In combination with bellows, this yields the additional advantage in that the spring characteristic can be additionally influenced.

In a still further embodiment, the middle part comprises a spring that is arranged coaxially and acts as both a tension spring and a compression spring. Therefore, the helical spring may also absorb torsional forces.

In a yet further embodiment, only the springs are in contact with both apposition plates up to an axial spring deflection $X \neq 0$. The advantage that can be achieved lies in the progressive spring characteristic. The second spring may also serve as a centering means for the cup springs. Additional advantages are that any particles formed by abrasion cannot escape into the patient's body. This embodiment also allows an extension/flexion movement with a low stiffness and provides protection against the growth of connective tissue into the prosthesis.

In another embodiment, the middle part also has a jacket comprised of bellows on the outside. This jacket provides protection against the penetration of bodily fluids.

In still another embodiment, the middle part is detachably connected to the two apposition plates via a snap closure.

In yet another embodiment, the apposition plates are connected to the middle part via friction bearings which are preferably made of a ceramic material. The friction bearings are advantageously designed so that the apposition plates can execute a limited translational motion across the longitudinal axis with respect to the middle part.

The translational motion preferably amounts to +/−0.5 mm. Thus, all six degrees of freedom are accounted for by the friction bearing and the receptacles of the cup springs and the possible rotation of approx. +/−30° about the longitudinal axis of the prosthesis.

In another embodiment, the cup springs have a stop which limits their compressibility. The stop protects the cup springs from overstressing. Therefore, higher forces can be absorbed without overloading the cup springs.

BRIEF DESCRIPTION OF THE DRAWINGS

The invention and its embodiments are explained in greater detail below on the basis of the partially schematic diagrams of several exemplary embodiments.

DETAILED DESCRIPTION OF THE INVENTION

Figure 1:
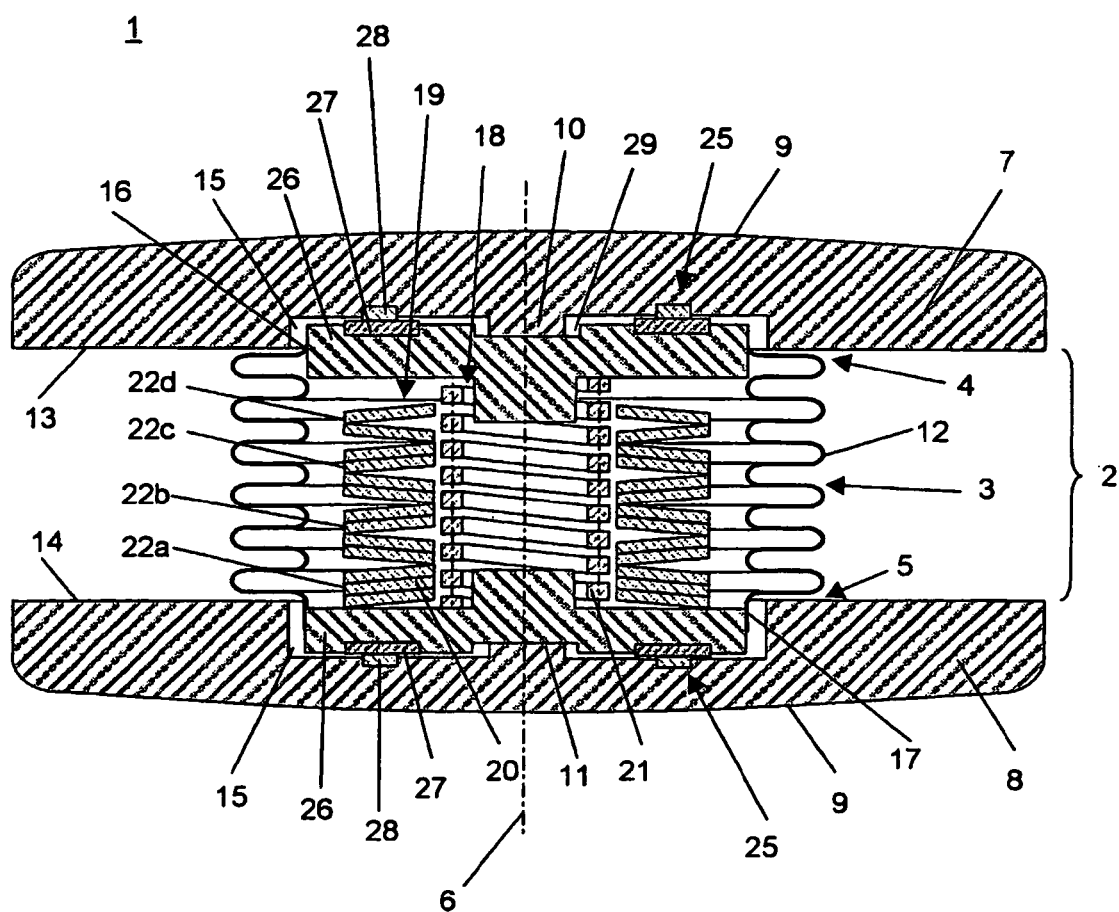
FIG. 1 shows a mediolateral section through an embodiment of a prosthetic intervertebral disk of the invention.

The embodiment of the prosthetic intervertebral disk 1 illustrated in FIG. 1 comprises a hollow cylindrical elastic middle part 2 having a jacket 3 designed as bellows 21, an upper end 4, a lower end 5, a central longitudinal axis 6, an upper apposition plate 7, and a lower apposition plate 8. Upper apposition plate 7 is arranged across longitudinal axis 6 at upper end 4 of middle part 2 and is suitable for coming in contact with the lower plate of a vertebra. Lower apposition plate 8 is arranged across longitudinal axis 6 at lower end 5 of middle part 2 and is suitable for coming in contact with the upper plate of a vertebra. The two apposition plates 7; 8 have a surface 9 with a convex curvature and axial pins 10 and 11 pointing inward. The jacket 3 in this embodiment includes bellows 12, which are attached to the two apposition plates 7; 8. Depending on the material, the bellows 12 may be welded, glued, or pressed to apposition plates 7; 8.

Upper apposition plate 7 has a lower surface 13 facing middle part 2, and similarly, lower apposition plate 8 has an upper surface 14 facing middle part 2. The lower and upper surfaces 13,14 each have a groove 15 arranged in a circle to receive the upper plates 26 attached to ends 16,17 of bellows 12. The pins 10,11 protrude coaxially with longitudinal axis 6 into recesses 29 on the exterior surfaces of upper plates 26, the recesses being concentric with the longitudinal axis 6. For the apposition plates 7,8 to be laterally displaceable in relation to middle part 2, recesses 29 have a larger diameter across longitudinal axis 6 than pins 10,11, which are movable therein on apposition plates 7,8. The outer ring elements 28, which are inserted concentrically with longitudinal axis 6 into circular grooves 15 in lower and upper surfaces 13,14 of apposition plates 7,8, rest on the inner ring elements 27 inserted into the outer surfaces of the upper plates 26. The inner and outer ring elements 27,28, which rest in pairs one on the other each form a friction bearing 25 such that apposition plates 7,8 are displaceable laterally within the play allowed by pins 10,11 and the recesses 29 in relation to middle part 2.

Elastic means 19, which are assembled from cup springs 20, are arranged around a helical spring 21. In the embodiment illustrated here, only helical spring 21 is in contact with the two upper plates 26 in the no-load state of the prosthetic intervertebral disk 1. Thus, only helical spring 21 is at first compressed when there is load on the prosthetic intervertebral disk. After a spring deflection s=X, elastic means 19 also come in contact with both apposition plates 7,8, so that with a further displacement of the two apposition plates 7,8 toward one another, s>X, a higher spring rate becomes effective. In the embodiment shown here, the elastic means 19 are comprised of cup spring assemblies 22a, 22b, 22c, 22d with identical cup springs 20. But the first cup spring assembly 22a has a cup spring assembly comprising three stacked-cup springs 20 pointing in the same direction, the second and third cup spring assemblies 22b; 22c each having two oppositely directed groups of two stacked-cup springs 20 facing in the same direction. The fourth cup spring assembly 22d has two cup springs 20 directed in opposite directions. A progressive spring characteristic of elastic means 19 is achieved because of this design of the cup spring assemblies 22a, 22b, 22c, 22d.

Figure 2:
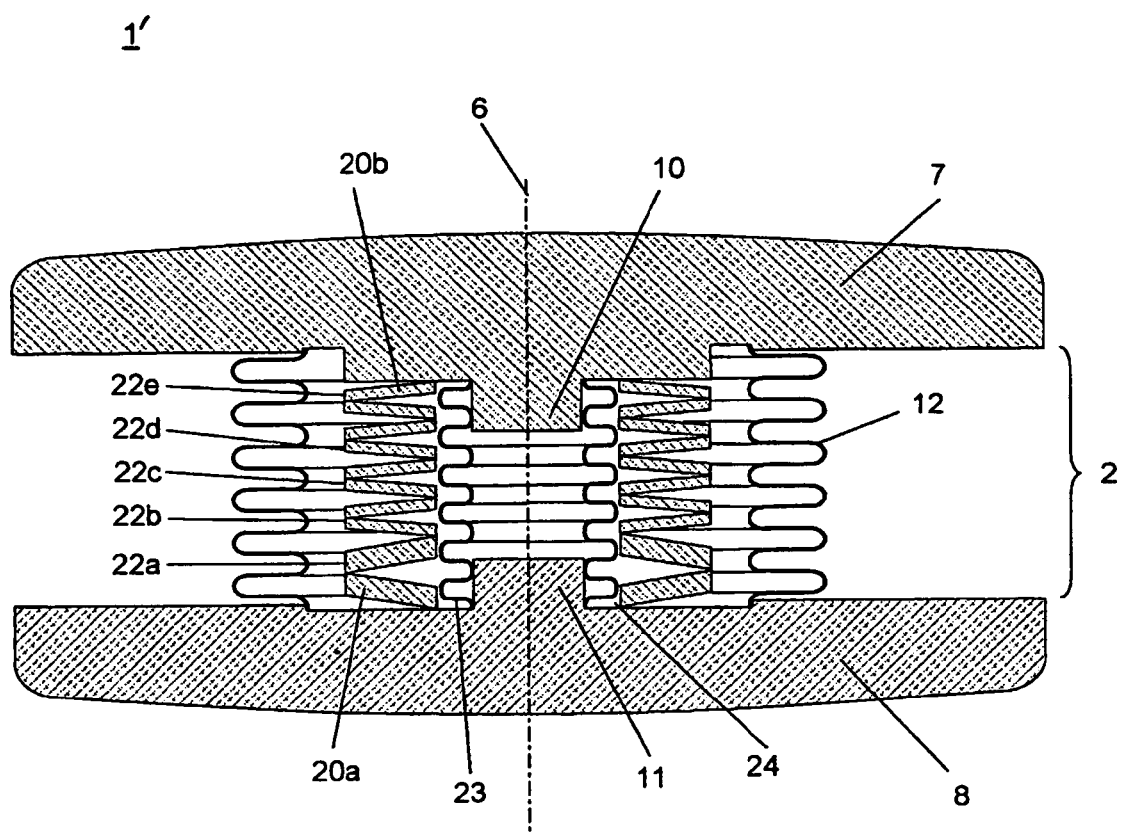
FIG. 2 shows a mediolateral section through another embodiment of a prosthetic intervertebral disk of the invention.

The embodiment of the prosthetic intervertebral disk 1' illustrated in FIG. 2 differs from the embodiment illustrated in FIG. 1 in that, firstly, instead of spring 18, an internal bellows 23 is arranged between apposition plates 7,8. Secondly, elastic means 19 comprises a first cup spring assembly 22a having first cup springs 20a and four additional cup spring assemblies 22b,22c,22d,22e having second cup springs 22b. Thirdly, middle part 2 is attached to apposition plates 7,8 without upper plates 26 (FIG. 1). The first cup springs 20a have a greater stiffness than the second cup springs 20b, so elastic means 19 has a progressive spring characteristic. The internal bellows 23 are guided through bores 24 in cup springs 20 in parallel with longitudinal axis 6 and serve as a centering means for cup springs 20. The internal bellows 23 are flexible axially and in bending, so that apposition plates 7,8 can also be moved obliquely with respect to one another and longitudinal axis 6 can be curved within a conical area.

We claim:

1. A prosthetic intervertebral disk or intervertebral implant having a central longitudinal axis, the disk comprising:

an upper apposition plate arranged across the longitudinal axis, the upper apposition plate including an upper surface suitable for contacting a lower plate of a first vertebra and a lower surface opposite the upper surface, the lower surface including a groove formed therein and a pin extending from the lower surface of the upper apposition plate, the pin being located within the groove formed in the lower surface of the upper apposition plate;

an intermediate upper plate member arranged across the longitudinal axis, the intermediate upper plate member being receivable within the groove formed in the lower surface of the upper apposition plate, the intermediate upper plate member including an upper surface and a lower surface opposite the upper surface, the upper surface of the intermediate upper plate member including a groove for receiving the pin extending from the lower surface of the upper apposition plate, the upper surface of the intermediate upper plate member being coupled to the lower surface of the upper apposition plate within the groove via friction bearings so that the intermediate upper plate member can translate with respect to the upper apposition plate, the lower surface of the intermediate upper plate member including a pin extending therefrom;

a lower apposition plate arranged across the longitudinal axis, the lower apposition plate including a lower surface suitable for contacting an upper plate of a second vertebra and an upper surface opposite the lower surface, the upper surface including a groove formed therein and a pin extending from the upper surface of the lower apposition plate, the pin being located within the groove formed in the upper surface of the lower apposition plate;

an intermediate lower plate member arranged across the longitudinal axis, the intermediate lower plate member being receivable within the groove formed in the upper surface of the lower apposition plate, the intermediate lower plate member including a lower surface and an upper surface opposite the lower surface, the lower surface of the intermediate lower plate member including a groove for receiving the pin extending from the upper surface of the lower apposition plate, the lower surface of the intermediate lower plate member being coupled to the upper surface of the lower apposition plate within the groove via friction bearings so that the intermediate lower plate member can translate with respect to the lower apposition plate, the upper surface of the intermediate lower plate member including a pin extending therefrom;

a helical spring including a bore extending therethrough for receiving the pin extending from the lower surface of the intermediate upper plate member and the pin extending from the upper surface of the intermediate lower plate member so that the helical spring operatively couples the intermediate upper and lower plate members in a no-load state;

a second elastic means operatively coupled to one of the lower surface of the intermediate upper plate member and the upper surface of the intermediate lower plate member and spaced by a distance from the other one of the lower surface of the intermediate upper plate member and the upper surface of the intermediate lower plate member in the no-load state, the second elastic means coming into contact with the both the lower surface of the intermediate upper plate member and the upper surface of the intermediate lower plate member when the helical spring is compressed by a distance X; and a jacket circumferentially disposed about the helical spring and the second elastic means, the jacket operatively associated with the upper and lower apposition plates.

2. The prosthetic intervertebral disk of claim 1 wherein the second elastic means is arranged coaxially about the helical spring.

3. The prosthetic intervertebral disk of claim 2 wherein the second elastic means is a plurality of cup springs joined together to form a cup spring assembly having a plurality of cup springs stacked together and pointing in the same direction.

4. The prosthetic intervertebral disk of claim 1 wherein the friction bearings are made of a ceramic material.

\* \* \* \* \*